(12) United States Patent
Zhang et al.

(10) Patent No.: US 12,414,951 B2
(45) Date of Patent: Sep. 16, 2025

(54) USE OF COMPOUND IN PREPARATION OF MEDICAMENT FOR PROPHYLAXIS AND TREATMENT OF INFLAMMATORY TISSUE DAMAGE

(71) Applicants: Sichuan University, Chengdu (CN); Nuclear Industry 416 Hospital, Chengdu (CN)

(72) Inventors: Shuyu Zhang, Chengdu (CN); Fenghao Geng, Chengdu (CN); Jianhui Chen, Chengdu (CN); Xiaoqian Li, Chengdu (CN)

(73) Assignees: Sichuan University, Chengdu (CN); Nuclear Industry 416 Hospital, Chengdu (CN)

( * ) Notice: Subject to any disclaimer, the term of this patent is extended or adjusted under 35 U.S.C. 154(b) by 103 days.

(21) Appl. No.: 18/156,095

(22) Filed: Jan. 18, 2023

(65) Prior Publication Data
US 2024/0016806 A1     Jan. 18, 2024

(30) Foreign Application Priority Data

Jul. 18, 2022     (CN) .......................... 202210839676.4

(51) Int. Cl.
| | |
|---|---|
| *A61K 31/517* | (2006.01) |
| *A61P 17/02* | (2006.01) |
| *A61P 17/16* | (2006.01) |
| *A61P 17/18* | (2006.01) |
| *A61P 29/00* | (2006.01) |
| *A61P 39/00* | (2006.01) |

(52) U.S. Cl.
CPC ............ *A61K 31/517* (2013.01); *A61P 17/02* (2018.01); *A61P 17/16* (2018.01); *A61P 17/18* (2018.01); *A61P 29/00* (2018.01); *A61P 39/00* (2018.01)

(58) Field of Classification Search
CPC ........ A61K 31/517; A61P 39/00; A61P 17/02; A61P 17/16; A61P 17/18; A61P 29/00
See application file for complete search history.

(56) References Cited

PUBLICATIONS

Vignola, A.M., Kips, J. and Bousquet, J., 2000. Tissue remodeling as a feature of persistent asthma. Journal of Allergy and Clinical Immunology, 105(6), pp. 1041-1053. (Year: 2000).*
Park, K.C. and Han, W.S., 2002. Viral skin infections: diagnosis and treatment considerations. Drugs, 62, pp. 479-490. (Year: 2002).*
Stone, H.B., Coleman, C.N., Anscher, M.S. and McBride, W.H., 2003. Effects of radiation on normal tissue: consequences and mechanisms. The lancet oncology, 4(9), pp. 529-536. (Year: 2003).*
Sina, B., Kao, G.F., Deng, A.C. and Gaspari, A.A., 2009. Skin biopsy for inflammatory and common neoplastic skin diseases: optimum time, best location and preferred techniques. A critical review. Journal of cutaneous pathology, 36(5), pp. 505-510. (Year: 2009).*
Ryan, J.L., 2012. Ionizing radiation: the good, the bad, and the ugly. Journal of Investigative Dermatology, 132(3), pp. 985-993. (Year: 2012).*
Tabas, I. and Glass, C.K., 2013. Anti-inflammatory therapy in chronic disease: challenges and opportunities. Science, 339(6116), pp. 166-172. (Year: 2013).*
Dainichi, T., Hanakawa, S. and Kabashima, K., 2014. Classification of inflammatory skin diseases: a proposal based on the disorders of the three-layered defense systems, barrier, innate immunity and acquired immunity. Journal of dermatological science, 76(2), pp. 81-89. (Year: 2014).*
Kim et al. 2014. Radiation oncology journal, 32(3), p. 103 (Year: 2014).*
Zhao, G.N., Jiang, D.S. and Li, H., 2015. Interferon regulatory factors: at the crossroads of immunity, metabolism, and disease. Biochimica et Biophysica Acta (BBA)—Molecular Basis of Disease, 1852(2), pp. 365-378. (Year: 2015).*
Zhang, X.J., Jiang, D.S. and Li, H., 2015. The interferon regulatory factors as novel potential targets in the treatment of cardiovascular diseases. British journal of pharmacology, 172(23), pp. 5457-5476. (Year: 2015).*
Owlia, M.B., 2016. Tissue response to injury: Ubiquity of cell injury makes inflammation-mediated disorders ubiquitous. European Journal of Inflammation, 14(3), pp. 212-213. (Year: 2016).*

(Continued)

*Primary Examiner* — James H Alstrum-Acevedo
*Assistant Examiner* — Carolyn L. Ladd
(74) *Attorney, Agent, or Firm* — Fox Rothschild LLP

(57) ABSTRACT

The present disclosure relates to use of a compound in preparation of a medicament for prophylaxis and treatment of inflammatory tissue damage. The present disclosure provides use of a compound in preparation of a medicament for prophylaxis and treatment of tissue damage, and the compound has a structure represented by formula I. The compound having the structure represented by formula I provided by the present disclosure can inhibit transcriptional activity of interferon regulatory factor 1 (IRF1), have prophylactic and therapeutic effects on tissue damage, enhance cell proliferation ability after tissue cell injury, and repair injured tissues. The compound having the structure represented by formula I provided by the present disclosure has important significance and application value in the preparation of the medicament for prophylaxis and treatment of tissue damage, particularly in the preparation of a medicament for inflammatory injuries of skin tissues induced by radiation and/or oxidation.

Formula I

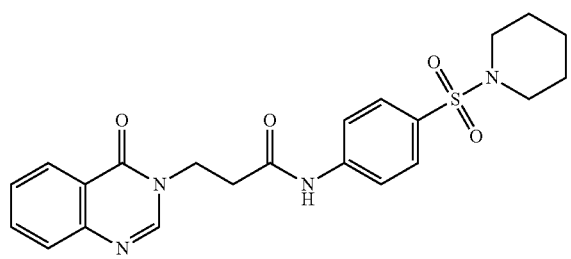

2 Claims, 7 Drawing Sheets

(56) References Cited

PUBLICATIONS

He, S. and Sharpless, N.E., 2017. Senescence in health and disease. Cell, 169(6), pp. 1000-1011. (Year: 2017).*

Seite, S., Bensadoun, R.J. and Mazer, J.M., 2017. Prevention and treatment of acute and chronic radiodermatitis. Breast cancer: targets and therapy, pp. 551-557. (Year: 2017).*

Schett, G. and Neurath, M.F., 2018. Resolution of chronic inflammatory disease: universal and tissue-specific concepts. Nature communications, 9(1), p. 3261. (Year: 2018).*

Thompson, C.D., Matta, B. and Barnes, B.J., 2018. Therapeutic targeting of IRFs: pathway-dependence or structure-based?. Frontiers in immunology, 9, p. 2622. (Year: 2018).*

Anatomy & Physiology. 2019 by Lindsay M. Biga, Staci Bronson, Sierra Dawson, Amy Harwell, Robin Hopkins, Joel Kaufmann, Mike LeMaster, Philip Matern, Katie Morrison-Graham, Kristen Oja, Devon Quick, Jon Runyeon (Year: 2019).*

Hanania, A.N., Mainwaring, W., Ghebre, Y.T., Hanania, N.A. and Ludwig, M., 2019. Radiation-induced lung injury: assessment and management. Chest, 156(1), pp. 150-162. (Year: 2019).*

Armstrong, A.W. and Read, C., 2020. Pathophysiology, clinical presentation, and treatment of psoriasis: a review. Jama, 323(19), pp. 1945-1960. (Year: 2020).*

Boice, A. and Bouchier-Hayes, L., 2020. Targeting apoptotic caspases in cancer. Biochimica et Biophysica Acta (BBA)—Molecular Cell Research, 1867(6), p. 118688. (Year: 2020).*

Carafa, V. and Altucci, L., 2020. Deregulation of cell death in cancer: Recent highlights. Cancers, 12(12), p. 3517. (Year: 2020).*

Dicarlo, A.L., Bandremer, A.C., Hollingsworth, B.A., Kasim, S., Laniyonu, A., Todd, N.F., Wang, S.J., Wertheimer, E.R. and Rios, C.I., 2020. Cutaneous radiation injuries: models, assessment and treatments. Radiation research, 194(3), pp. 315-344. (Year: 2020).*

Vidoni, C., Ferraresi, A., Secomandi, E., Vallino, L., Dhanasekaran, D.N. and Isidoro, C., Nov. 2020, Epigenetic targeting of autophagy for cancer prevention and treatment by natural compounds. In Seminars in cancer biology (vol. 66, pp. 34-44). Academic Press. (Year: 2020).*

Lei et al. 2020. Frontiers in Immunology, 11, p. 593901 (Year: 2020).*

Feng, H., Zhang, Y.B., Gui, J.F., Lemon, S.M. and Yamane, D., 2021. Interferon regulatory factor 1 (IRF1) and anti-pathogen innate immune responses. PLoS pathogens, 17(1), p. e1009220. (Year: 2021).*

Tuieng, R.J., Cartmell, S.H., Kirwan, C.C. and Sherratt, M.J., 2021. The effects of ionising and non-ionising electromagnetic radiation on extracellular matrix proteins. Cells, 10(11), p. 3041. (Year: 2021).*

Yang, F., Bettadapura, S.N., Smeltzer, M.S., Zhu, H. and Wang, S., 2022. Pyroptosis and pyroptosis-inducing cancer drugs. Acta Pharmacologica Sinica, 43(10), pp. 2462-2473. (Year: 2022).*

\* cited by examiner

USE OF COMPOUND IN PREPARATION OF MEDICAMENT FOR PROPHYLAXIS AND TREATMENT OF INFLAMMATORY TISSUE DAMAGE

CROSS-REFERENCE TO RELATED APPLICATION

This patent application claims the benefit and priority of Chinese Patent Application No. 202210839676.4, filed with the China National Intellectual Property Administration on Jul. 18, 2022, the disclosure of which is incorporated by reference herein in its entirety as part of the present application.

TECHNICAL FIELD

The present disclosure belongs to the technical field of biomedicine, and specifically relates to use of a compound in preparation of a medicament for prophylaxis and treatment of inflammatory tissue damage.

BACKGROUND

Skin is the body's largest tissue and organ. Radiation-induced skin injury, the most common complication in tumor radiotherapy and radiation accidents, is characterized by rapid progression, heavy damage, and difficult healing, and no specific prophylactic and therapeutic drug is available at present. It is indicated that ionizing radiation, virus infection, and chemotherapeutics can cause tissue cell pyroptosis, necrosis, and inflammation-induced death, leading to tissue damage. When the body experiences stimuli such as ionizing radiation (damage-related biological pattern) and microbe (virus) infection (pathogen-related biological pattern), immune response is excessively activated to form "inflammation storm" and aggravate the tissue damage.

Interferon regulatory factor 1 (IRF1) is not only a transcription factor, but also act as a tumor suppressor. Activated IRF1 can influence the expression of downstream interferons and interferon-stimulated genes (ISGs) through transcriptional regulation, and participate in the regulation of innate immunity, acquired immunity, stress responses of the body against bacteria and viruses, cell proliferation and apoptosis, DNA damage repair, inhibition of tumor growth, promotion of tumor immune response, and other important functions. However, excessive activation of IRF1 caused by external stimuli (for example, ionizing radiation and virus infection) is an important cause of severe inflammatory response in tissue and further inflammatory tissue damage.

SUMMARY

An objective of the present disclosure is to provide use of a compound in preparation of a medicament for prophylaxis and treatment of inflammatory tissue damage. The compound having the structure represented by formula I provided by the present disclosure has a prophylactic effect on the tissue damage, and can effectively alleviate the progression of the tissue damage.

To achieve the above objective, the present disclosure provides the following technical solutions:

The present disclosure provides use of a compound in preparation of a medicament for prophylaxis and treatment of tissue damage, and the compound has a structure represented by formula I:

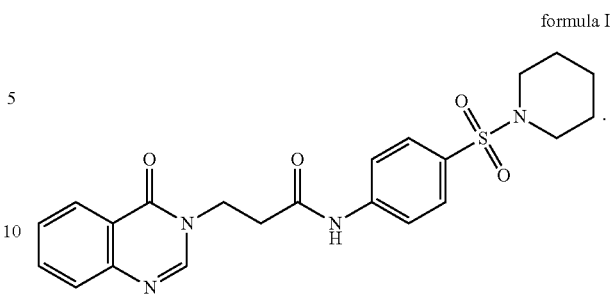

formula I

Preferably, the tissue damage may be caused by excessive inflammatory response activated by IRF1.

Preferably, the tissue damage may be skin tissue damage.

Preferably, the skin tissue damage may be radiation-induced skin injury.

Preferably, the radiation-induced skin injury may be ionizing radiation-induced skin injury.

Preferably, the skin tissue damage may be oxidative skin injury.

Preferably, the skin tissue damage may be virus-induced skin injury.

Preferably, the tissue damage may be ionizing radiation-induced lung tissue injury.

The present disclosure provides a medicament for prophylaxis and treatment of tissue damage, including a compound and pharmaceutical excipients, and the compound has a structure represented by formula I:

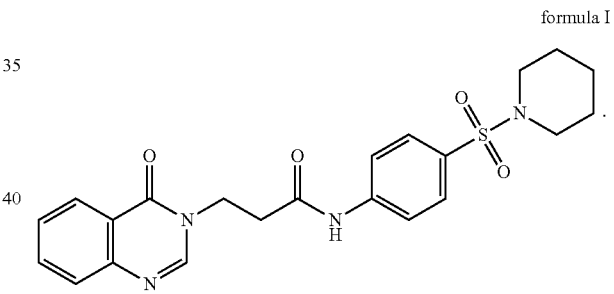

formula I

Preferably, dosage forms of the medicament for prophylaxis and treatment of tissue damage may include an injection, an ointment, or an aerosol.

Use of a compound in preparation of a medicament for prophylaxis and treatment of tissue damage is provided, and the compound has a structure represented by formula I:

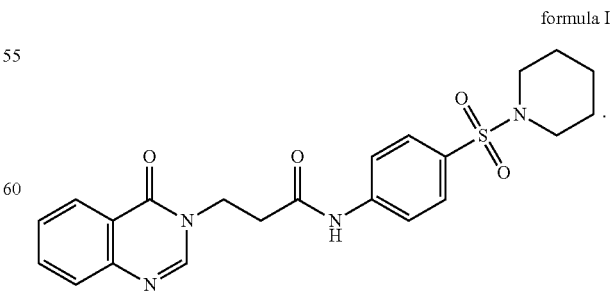

formula I

The compound having the structure represented by formula I provided by the present disclosure (named IRSKIN- 1) can inhibit transcriptional activity of IRF1, have prophylactic and therapeutic effects on tissue damage caused by excessive inflammatory response activated by IRF1, enhance cell proliferation ability after inflammatory injury of tissue cells, and repair injured tissues. The compound having the structure represented by formula I provided by the present disclosure has important significance and application value in the preparation of the medicament for prophylaxis and treatment of tissue damage, particularly in the preparation of a medicament for inflammatory injuries of skin tissues induced by radiation and/or oxidation.

BRIEF DESCRIPTION OF THE DRAWINGS

in FIG. 8: IRSKIN-1 is dissolved in DMSO to prepare a 50 mM solution and subcutaneously injected 1 and 3 days before irradiation (100 µL/time), respectively, a control group is subcutaneously injected with equivalent DMSO solution, and photos of the progression of radiation-induced skin injury in the mice are taken at different time points after irradiation; in FIG. 8: panels (a) and (c) show DMSO-treated mice, panel (a) shows a condition at 15 days after irradiation, and panel (c) shows a condition at 30 days after irradiation; panels (b) and (d) show IRSKIN-1-treated mice, panel (b) shows a condition at 15 days after irradiation, and panel (d) shows a condition at 30 days after irradiation;

DETAILED DESCRIPTION OF THE EMBODIMENTS

Figure 1:
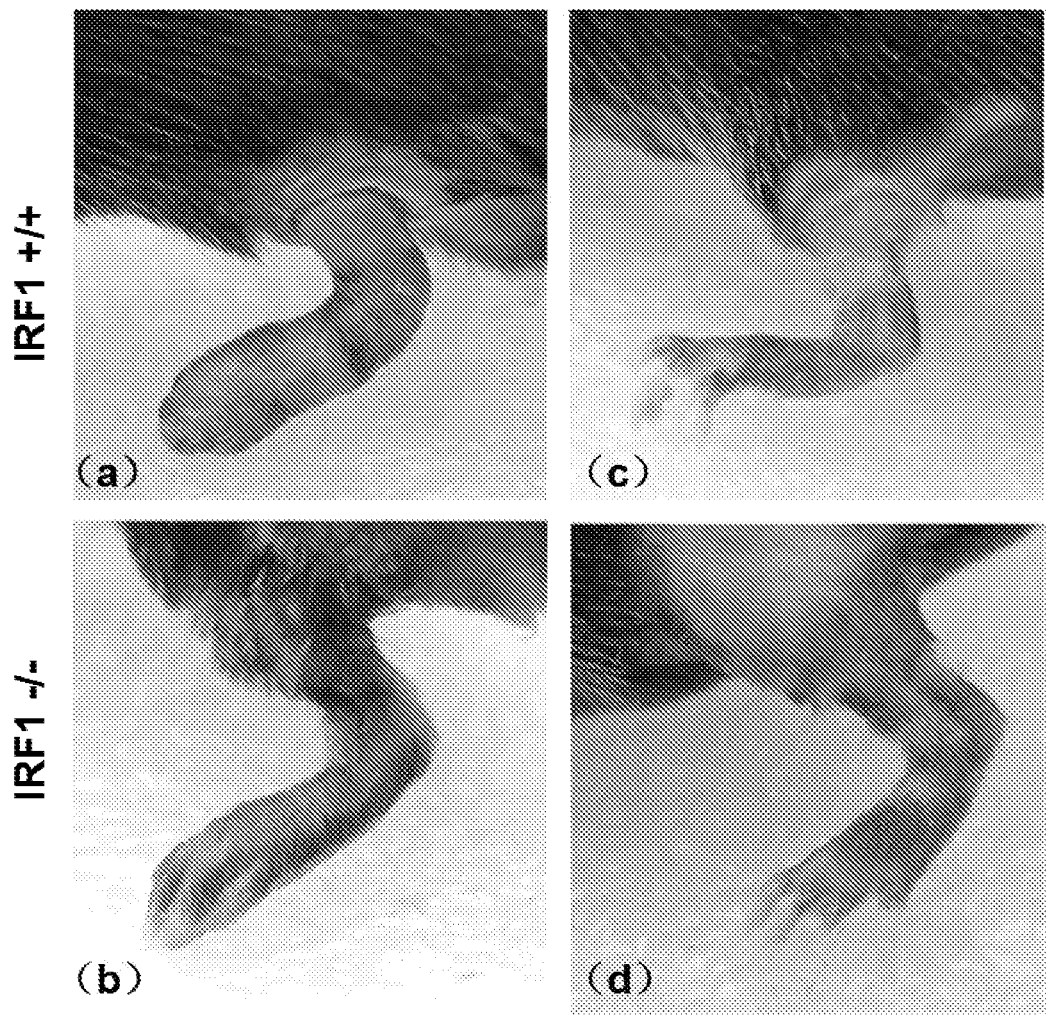
FIG. 1 illustrates post-irradiation skin injuries of IRF1 knockout mice, where in FIG. 1, panels (a) and (c) show wild-type mice, panel (a) shows a condition at 19 days after irradiation, and panel (c) shows a condition at 41 days after irradiation; panels (b) and (d) show IRF1 null mice, panel (b) shows a condition at 19 days after irradiation, and panel (d) shows a condition at 41 days after irradiation.

The present disclosure provides use of a compound in preparation of a medicament for prophylaxis and treatment of inflammatory tissue damage, and the compound has a structure represented by formula I:

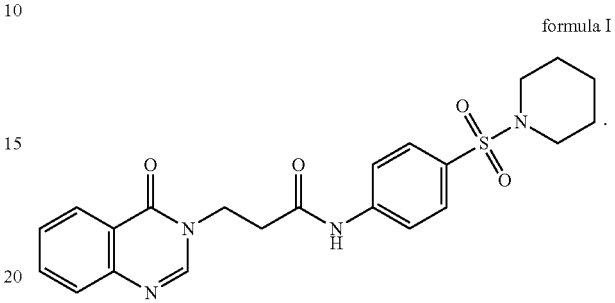

formula I

In the present disclosure, the compound having the structure represented by formula I is purchased from SPECS, Germany, the website is:

www.specs.net/
index.php?page=startpage&note=password %20 for %20user %20-%20zs huaijun % 20-%20correct.

In the present disclosure, the compound having the structure represented by formula I has the following drug ID number: AP-853/42423499.

In the present disclosure, the compound having the structure represented by formula I is named: 3-(4-oxo-3 (4H)-quinazolinyl)-N-[4-(1-piperidinylsulfonyl)phenyl]propanamide.

In the present disclosure, the compound having the structure represented by formula I has a chemical formula of $C_{22}H_{24}N_4O_4S$.

In the present disclosure, the compound having the structure represented by formula I is named: 3-(4-oxo-3 (4H)-quinazolinyl)-N-[4-(1-piperidinylsulfonyl)phenyl]propanamide.

In the present disclosure, the tissue damage may preferably be caused by excessive inflammatory response activated by IRF1.

In the present disclosure, the tissue damage may preferably be skin tissue damage.

In the present disclosure, the skin tissue damage may preferably be radiation-induced skin injury.

In the present disclosure, the radiation-induced skin injury may preferably be ionizing radiation-induced skin injury.

In the present disclosure, the skin tissue damage may preferably be oxidative skin injury.

In the present disclosure, the skin tissue damage may preferably be virus-induced skin injury.

In the present disclosure, the tissue damage may preferably be ionizing radiation-induced lung tissue injury.

The present disclosure provides use of a compound in preparation of a medicament for tissue regeneration and repair, and the compound has a structure represented by formula I:

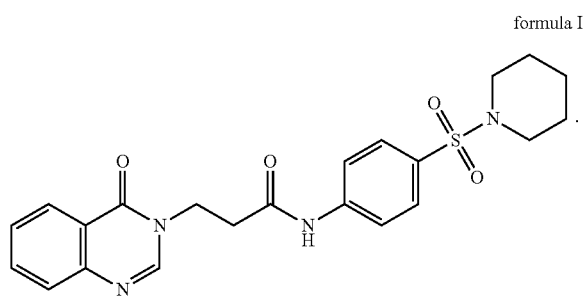 [SMILES: O=C(CCn1cnc2ccccc2c1=O)Nc1ccc(S(=O)(=O)N2CCCCC2)cc1]

formula I

In the present disclosure, the tissue regeneration and repair may preferably realize cell proliferation and differentiation and form new tissues at injured tissue sites containing the corresponding tissues.

The present disclosure provides a medicament for prophylaxis and treatment of tissue damage, including a compound and related pharmaceutical excipients. The compound has a structure represented by formula I:

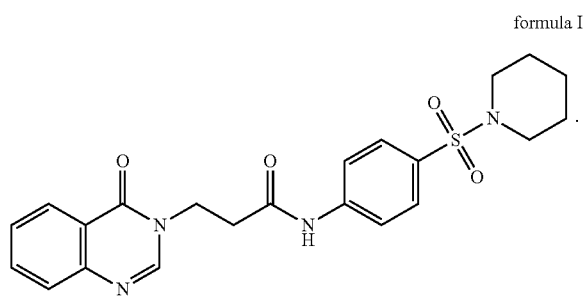 [SMILES: O=C(CCn1cnc2ccccc2c1=O)Nc1ccc(S(=O)(=O)N2CCCCC2)cc1]

formula I

In the present disclosure, the pharmaceutical excipients may preferably include one or more of pharmaceutically acceptable salts, excipients, and vehicles.

In the present disclosure, dosage forms of the medicament for prophylaxis and treatment of tissue damage may preferably include an injection, an ointment, or an aerosol.

In the present disclosure, in the medicament for prophylaxis and treatment of tissue damage, the compound having a structure represented by formula I may preferably have an in vitro effective concentration of 10-20 μmol/L.

In the present disclosure, in the medicament for prophylaxis and treatment of tissue damage, an effective subcutaneous injection dose of the compound having a structure represented by formula I may preferably be 100 μg/time×2 times.

In the present disclosure, the compound provided by the present disclosure (named IRSKIN-1), all reagents, cell lines, animals, and instrument are commercially available products.

In order to further illustrate the present disclosure, the foregoing technical solutions provided by the present disclosure will be described in detail below in conjunction with accompanying drawings and examples, but they should not be construed as limiting the protection scope of the present disclosure.

Example 1

Attenuation experiment of radiation-induced skin injury in the skin tissue of IRF1 knockout mice To determine the importance of IRF1 in the progression of radiation-induced skin injury, IRF1 knockout mice (stock number: 002762) were purchased from the Jackson Laboratory, the USA. After the IRF1 knockout mice were crossed with wild-type C57 mice, F2 wild-type IRF1 null mice were obtained by genotyping. Based on 1% of the body weight of each mouse, the mouse was anesthetized by intraperitoneal injection of 1% chloral hydrate, the skin of hind limbs of the mouse was depilated, and the mouse was immobilized on a board to reduce accidental movements during irradiation.

The skin of hind limbs of mice was irradiated with 6 MeV electron ray generated by linear accelerator (VARIAN 23EX Linear Accelerator, Varian Medical Systems Inc., the USA); the surface was covered with a 1 cm thick bolus, and non-irradiated sites were shielded with a lead plate; the irradiation area was approximately 25× 40 mm, the absorbed dose rate was 750 cGy/min, and the total dose was 35 Gy.

Figure 2:
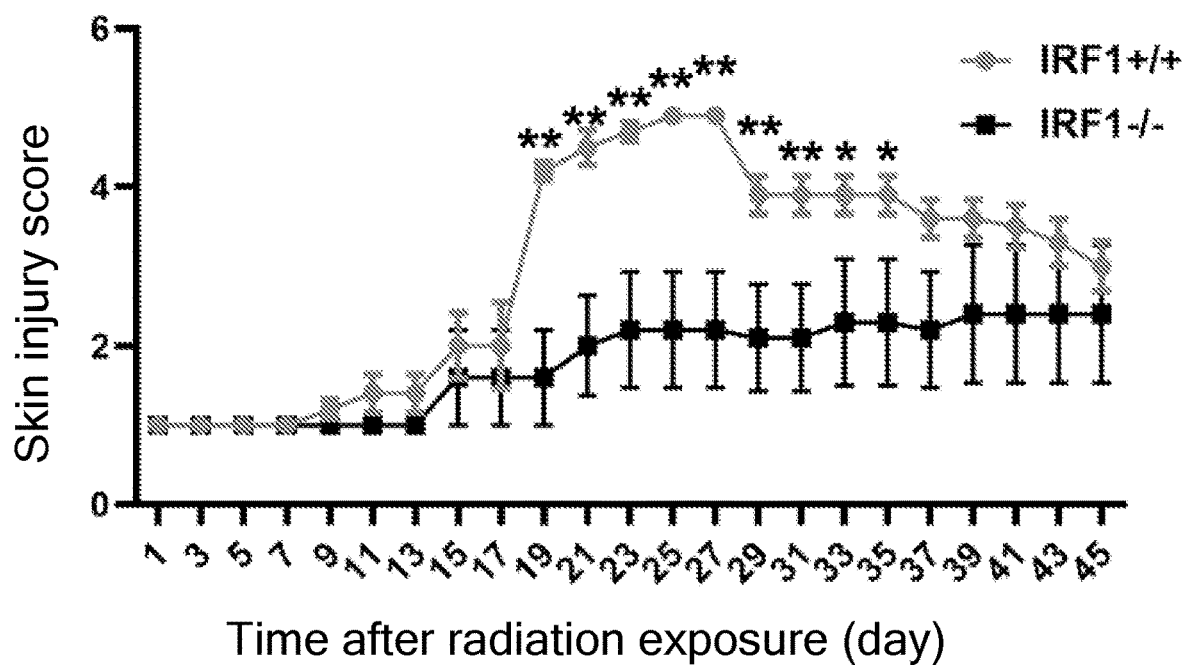
FIG. 2 illustrates scoring results of skin injuries of IRF1 wild-type and null mice.
Figure 3:
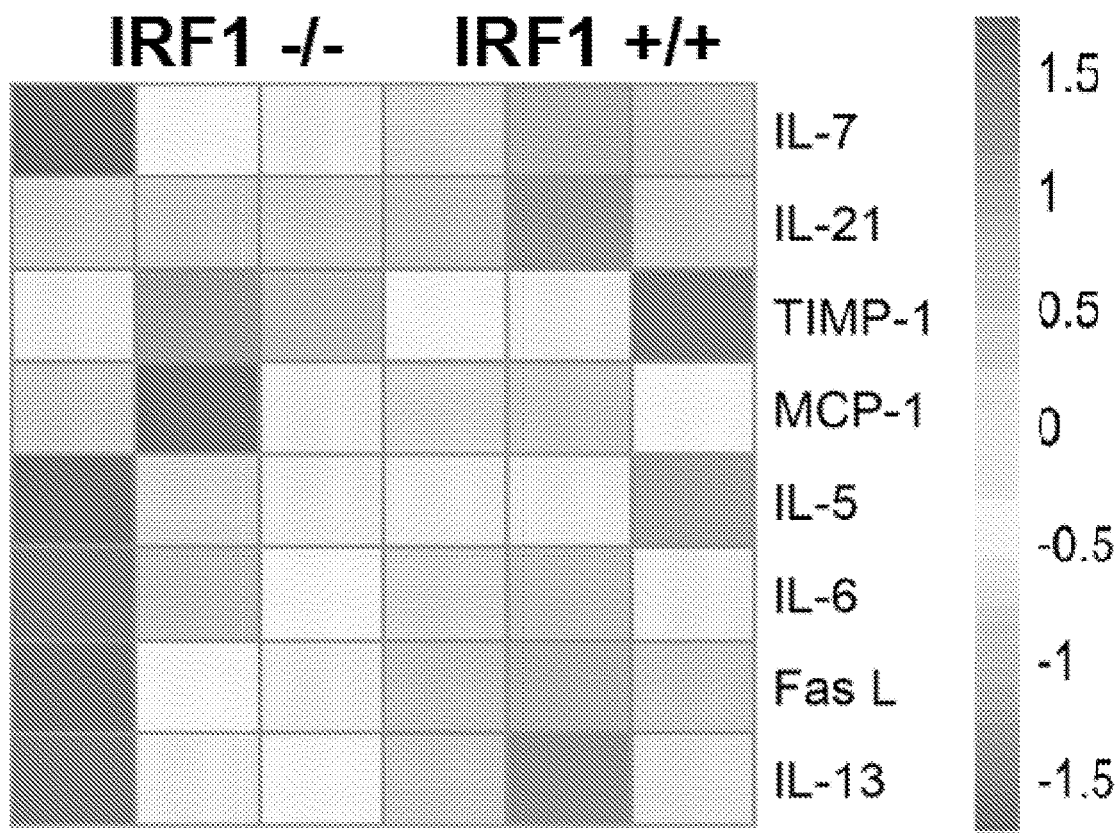
FIG. 3 illustrates microarray results of inflammatory factors of irradiated skin of IRF1 knockout mice.

The progression of the skin injury was observed: as shown in FIG. 1, 10 days after irradiation, control mice (wild-type) in panels (a) and (c) in FIG. 1 showed wet skin ulcers, whereas IRF1 knockout mice in panels (b) and (d) in FIG. 1 showed no skin injury. Scoring results of skin injuries of IRF1 wild-type and null mice are shown in FIG. 2 (** $P<0.01$, * $P<0.05$). The microarray results of inflammation are shown in FIG. 3. Results showed that the expression of inflammatory factors IL7, IL13, IL21, and Fas1 was significantly downregulated in the irradiated skin tissues of the IRF1 null mice.

Therefore, results in Example 1 indicated that IRF1 played a role in aggravating the inflammatory injury in the irradiated skin tissue; results in Example 1 further suggested that IRF1 inhibitor could enhance the radiation protection of the skin tissue. Based on this, the compound was screened by molecular docking, and the compound IRSKIN-1 screened in the present disclosure could inhibit the binding of IRF1 to DNA.

Example 2

Experiment of IRSKIN-1 inhibiting the transcriptional activity of IRF1

Figure 4:
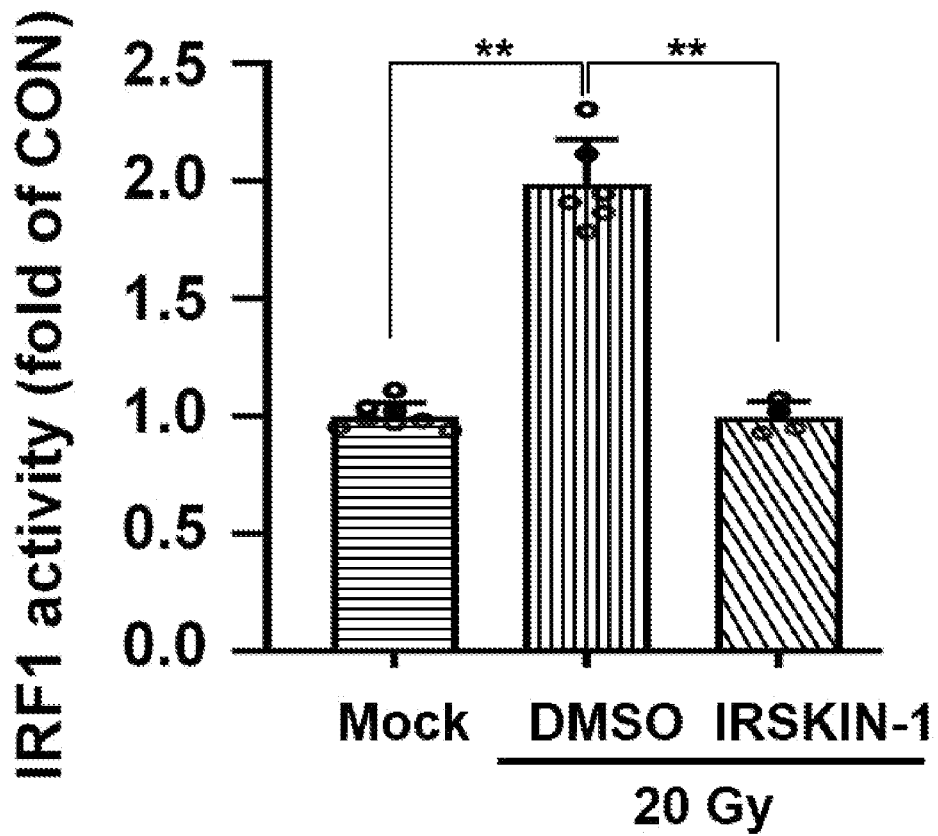
FIG. 4 illustrates results of research on a drug for effectively inhibiting transcriptional activity of IRF1 screened based on a dual-luciferase reporter system; where CON represents control group; Mock represents sham treatment group.

To determine the inhibitory effect of the compound (IRSKIN-1) on the transcriptional activity of IRF1, Hanbio Biotechnology (Shanghai) Co., Ltd. was entrusted to construct an h-IRF1 promoter-rluc adenovirus vector. The vector has four binding sites of IRF1, and the downstream of the promoter is a luciferase reporter gene. The virus was constructed based on a dual-luciferase reporter system, and the transcriptional activity of IRF1 could be directly reflected by the luciferase activity. Human skin keratinocytes (HaCaT cells) were infected in vitro according to a titer of 100 MOI, and the virus infection efficiency met the experimental requirement 48 h after infection. Groups included: a 0 Gy unirradiated group; an equivalent DMSO-treated irradiation group (X-ray, 20 Gy, dose rate 1.7 Gy/min), and an IRSKIN-1-treated irradiation group (treated with 10 μM IRSKIN-1 24 h before irradiation, as shown in FIG. 4, ** $P<0.01$).

A microplate reader PROMEGA and the corresponding substrates were used for detection 1 h after irradiation. The results are shown in FIG. 4. Ionizing radiation could lead to an increase in transcriptional activity of HaCaT cells, and the irradiated IRF1 activity was significantly lower in the IRSKIN-1-treated irradiation group than in the DMSO-treated irradiation group, indicating that this small molecule compound could effectively inhibit the transcriptional activity of IRF1 in the irradiated skin cells.

Example 3

Experiment of IRSKIN-1 promoting irradiated skin cell proliferation

To determine the promoting effect of IRF1 inhibitor IRSKIN-1 on irradiated skin cell proliferation, cells were treated with 10 μM IRSKIN-1 or equivalent DMSO for 24 h before irradiation, respectively; subsequently, the cells were subjected to fractionated irradiation at 2 Gy once or at 2 Gy twice or Sr 90 irradiation at 4 Gy once, respectively; subsequently, the effect of IRSKIN-1 on irradiated cell proliferation ability was evaluated by the colony formation test (2,500 cells were spread on each well of a 6-well plate).

Figure 5:
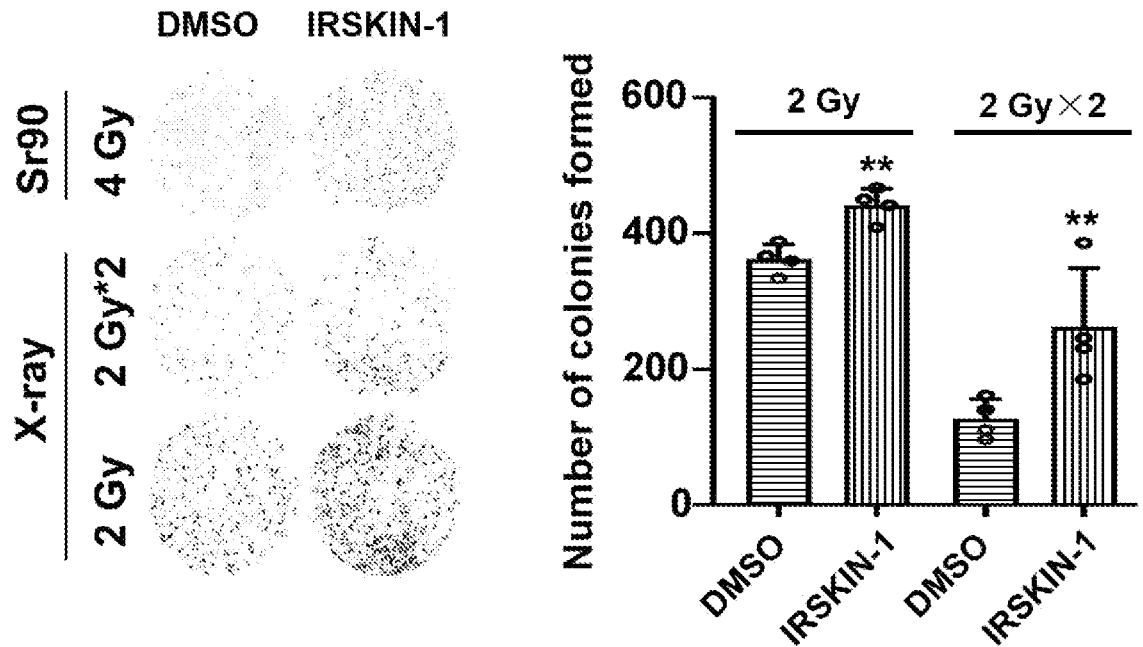
FIG. 5 illustrates research results of IRSKIN-1 promoting cell proliferation of irradiated skin.

Experimental results are shown in FIG. 5. Pretreatment with IRSKIN-1 could significantly improve the clone formation ability of skin cells irradiated by X-ray or Sr 90, indicating that IRSKIN-1 had a promoting effect on irradiated cell proliferation (** $P<0.01$).

Example 4

Experiment of IRSKIN-1 treatment reducing the mortality of irradiated cells

To determine whether IRSKIN-1 reduces the mortality of irradiated skin cells, cells were treated with 10 μM IRSKIN-1 or equivalent DMSO for 24 h before irradiation, respectively; subsequently, the cells were irradiated with 20 Gy X-ray once, and the effect of IRSKIN-1 on irradiated cell proliferation ability was evaluated by AV/PI staining method 3 days after irradiation.

Figure 6:
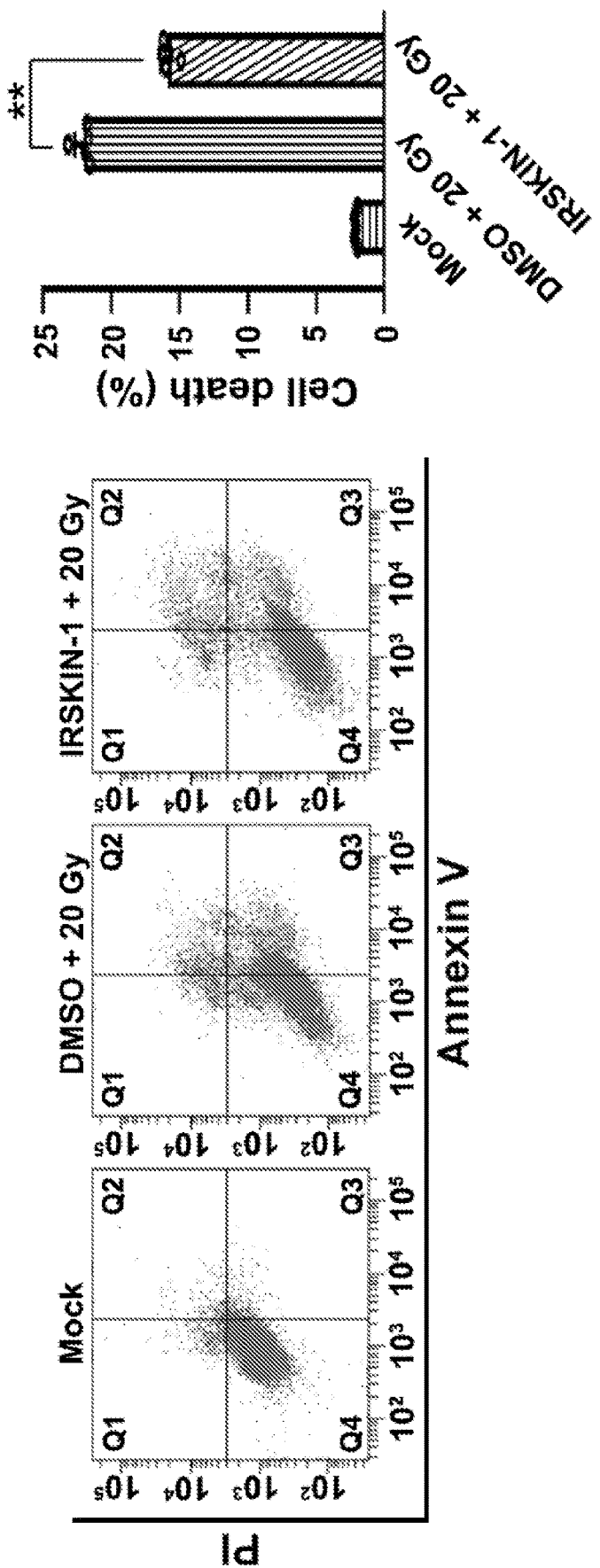
FIG. 6 illustrates research results of IRSKIN-1 reducing the mortality of irradiated cells after treatment of skin cells; where Mock represents sham treatment group.

Experimental results are shown in FIG. 6. Pretreatment with IRSKIN-1 could reduce cell mortality caused by skin cells X-ray irradiation, indicating that IRSKIN-1 played a role in reducing the mortality of irradiated cells (** $P<0.01$).

Example 5

Experiment of IRSKIN-1 treatment reducing the primary skin cell senescence rate of irradiated IRF1 wild-type mice To determine whether IRSKIN-1 reduces the senescence rate of irradiated skin cells, mouse primary skin cell were isolated and cultured, cells were treated with 10 μM IRSKIN-1 or equivalent DMSO for 24 h before irradiation, respectively; subsequently, the cells were irradiated with 20 Gy X-ray once, and the effect of IRSKIN-1 on irradiated primary cell senescence was evaluated by β-galactosidase staining method 3 days after irradiation.

Figure 7:
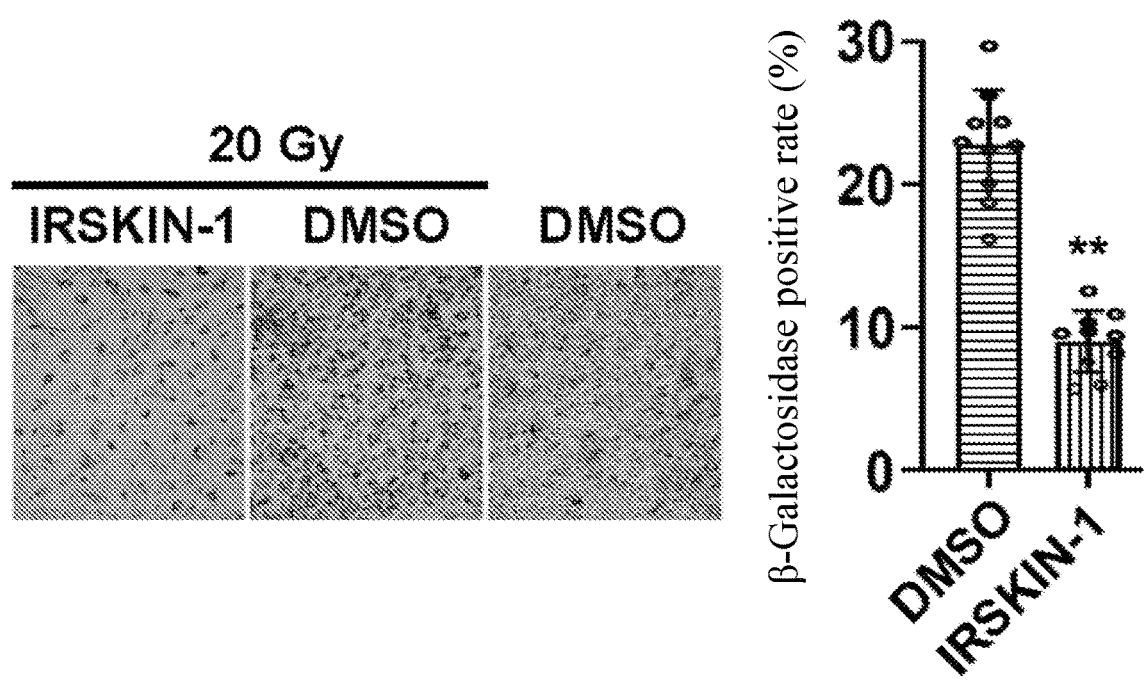
FIG. 7 illustrates research results of IRSKIN-1 treatment reducing the primary skin cell senescence rate of irradiated mice.

Experimental results are shown in FIG. 7. Pretreatment with IRSKIN-1 could reduce the β-galactosidase positive rate of mouse primary cells caused by X-ray irradiation (** $P<0.01$), indicating that IRSKIN-1 played a role in inhibiting the senescence of irradiated primary cells.

Example 6

Experiment of subcutaneous injection of IRSKIN-1 effectively alleviating the progression of radiation-induced skin injury in the mouse model Male C57 BL/6J mice aged 6-8 weeks were purchased from GemPharmatech Co., Ltd. The mice were acclimatized and randomized into two groups (6 mice per group); the mice were subcutaneously injected with IRSKIN-1 (which was dissolved in DMSO to prepare a 50 mM solution, 100 μL/time) and equivalent DMSO once 1 and 3 days before irradiation, respectively; based on 1% of the body weight of each mouse, the mouse was anesthetized by intraperitoneal injection of 1% chloral hydrate, the skin of hind limbs of the mouse was depilated, and the mouse was immobilized on a board to reduce accidental movements during irradiation.

The skin of limbs of mice was irradiated with 6 MeV electron ray generated by Varian 23EX Linear Accelerator (Varian, the USA); the surface was covered with a 1 cm thick bolus, and non-irradiated sites were shielded with a lead plate; the irradiation area was approximately 30×40 mm, the absorbed dose rate was 750 cGy/min, and the total dose was 45 Gy; and the range of the irradiated area was outlined with a marker pen during irradiation.

Figure 8:
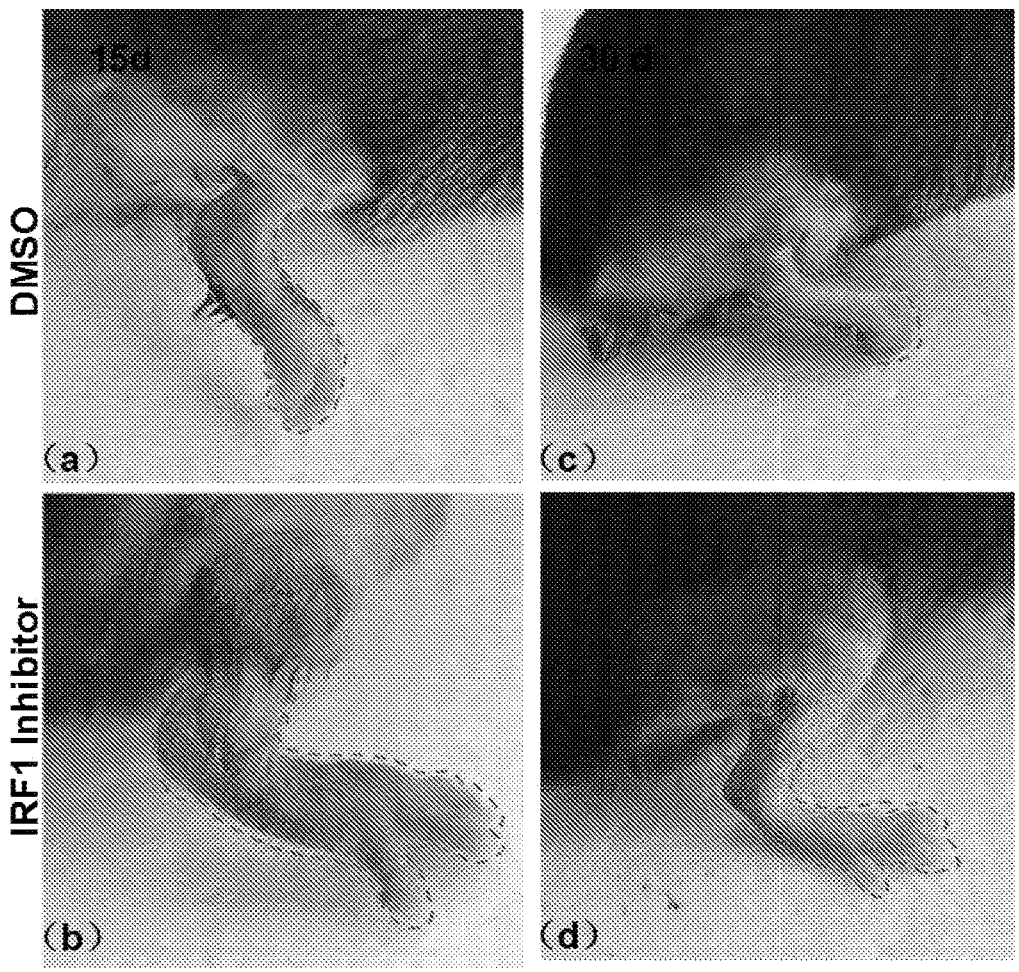
FIG. 8 illustrates results of respective effects of IRSKIN-1 and dimethyl sulfoxide (DMSO) treatments on progression of radiation-induced skin injury in mice.
Figure 9:
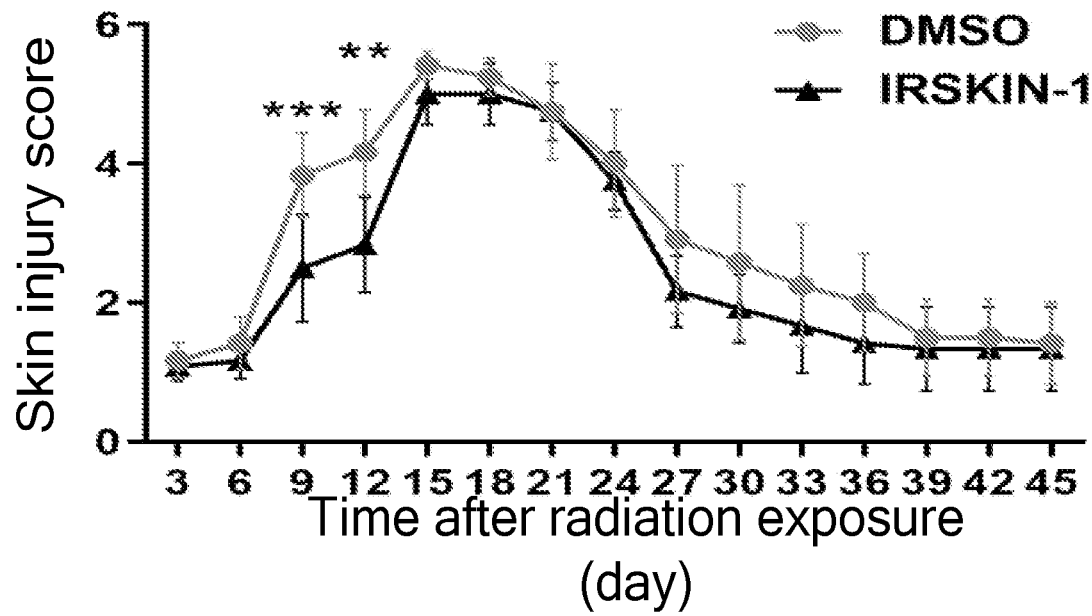
FIG. 9 illustrates effects of IRSKIN-1 and DMSO treatments on progression scores of radiation-induced skin injury in mice.
Figure 10:
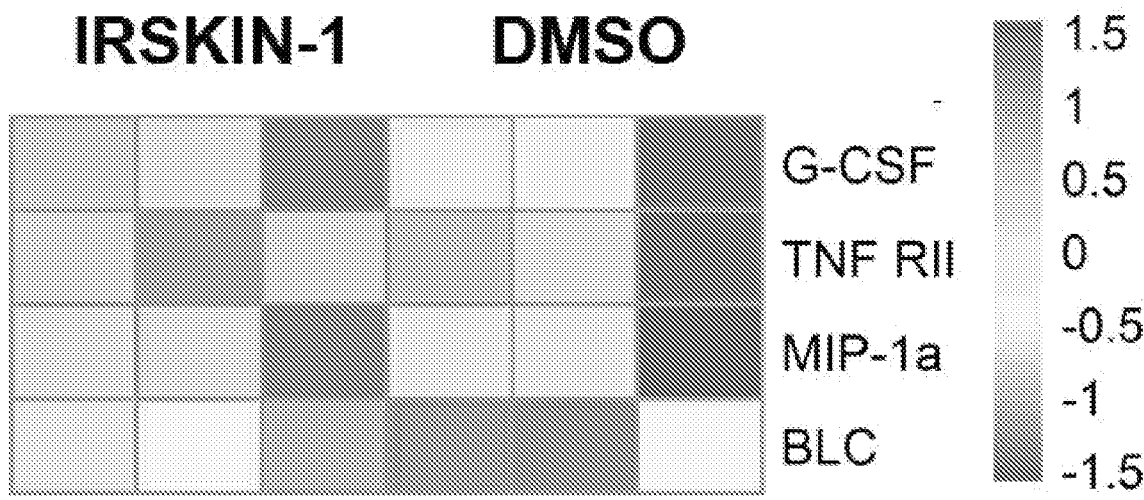
FIG. 10 illustrates microarray results of inflammation in irradiated mice treated with IRSKIN-1 and DMSO.

The skin injury was observed: results indicated that the progression of radiation-induced skin injury was slower in the mice of the IRSKIN-1 subcutaneous injection group than in those of the DMSO group, with a smaller ulcer wound area. As shown in FIG. 8, compared with skin wounds of both groups of mice, wet ulcers appeared in only fewer areas of the skin of the IRSKIN-1 treated mice, indicating subcutaneous injection of IRSKIN-1 played a role in alleviating the progression of radiation-induced skin injury in the mice. Results of IRSKIN-1 reducing progression scores of radiation-induced skin injury in the mice are shown in FIG. 9. Microarray results of inflammation are shown in FIG. 10. Results showed that the expression of G-CSF, TNF-R II, and MIP-1a was upregulated and the expression of BLC was downregulated in the skin tissue of the IRSKIN-1 treated mice.

Example 7

Inhibitory effect of IRSKIN-1 on expression of key regulatory proteins of inflammatory death in the irradiated skin To determine the mechanism of the inhibitory effect of IRF1 inhibitor IRSKIN-1 on inflammatory death in the irradiated skin cells, cells were treated with 10 μM IRSKIN-1 or equivalent DMSO for 24 h before irradiation, respectively; subsequently, the cells were irradiated with 20 Gy X-ray once, and changes in key proteins of cell pyroptosis pathway, Caspase1 and GSDMD, and inflammatory factor IL1 were detected by Western blot, so as to determine the inhibitory effect of IRSKIN-1 on inflammatory death in the irradiated skin cells and its mechanism.

Figure 11:
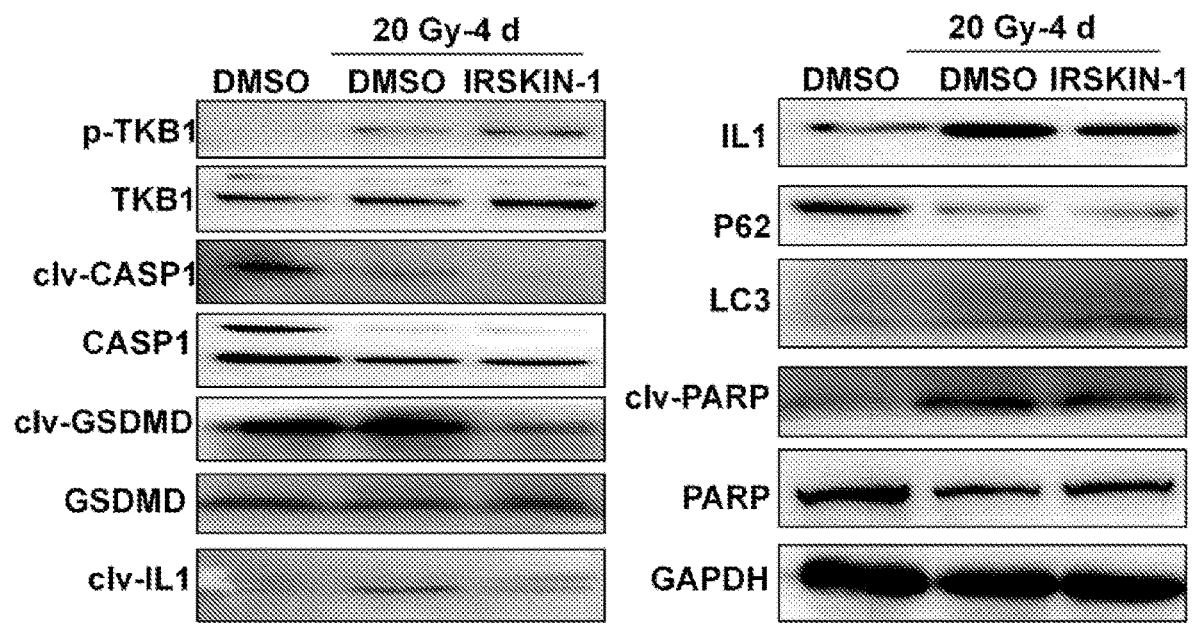
FIG. 11 illustrates test results of inhibitory effect of IRSKIN-1 on expression of key regulatory proteins of inflammatory death in the irradiated skin.
Figure 12:
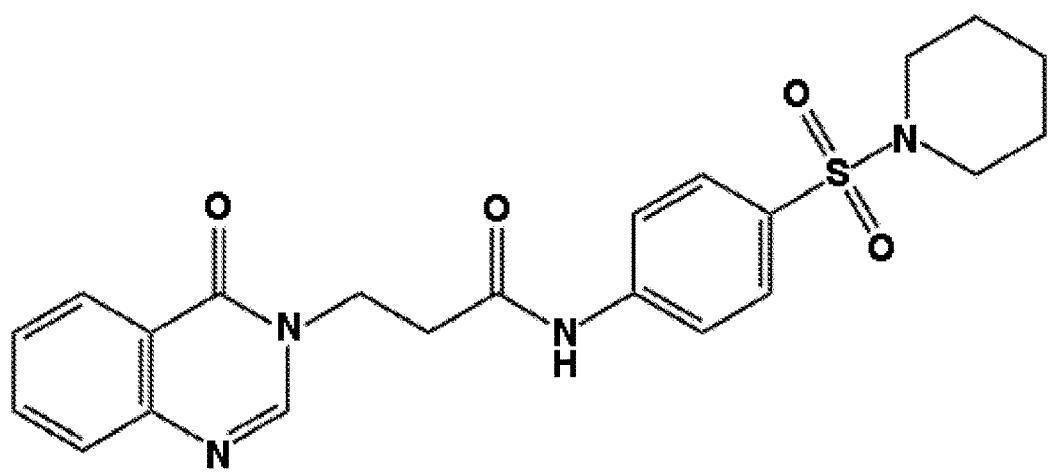
FIG. 12 illustrates a chemical structural formula of a compound having a structure represented by formula 1 provided by the present disclosure.

Experimental results are shown in FIG. 11. Pretreatment with IRSKIN-1 could inhibit the hydrolysis of Caspase1, GSDMD, and IL1 of skin cells, indicating that IRSKIN-1 had an inhibitory effect on the inflammatory death in the irradiated cells.

The above results indicated that the medicament played a role in alleviating the inflammatory injury of the skin after radiation exposure.

Although the present disclosure is described in detail in conjunction with the foregoing examples, they are only a part of, not all of, the examples of the present disclosure. Other examples can be obtained based on these examples without creative efforts, and all of these examples shall fall within the protection scope of the present disclosure.

What is claimed is:

1. A method for treating ionizing radiation-induced skin injury in a subject, comprising administering to the subject a pharmaceutical composition comprising a compound and one or more pharmaceutical excipients, wherein the compound has the structure represented by formula I:

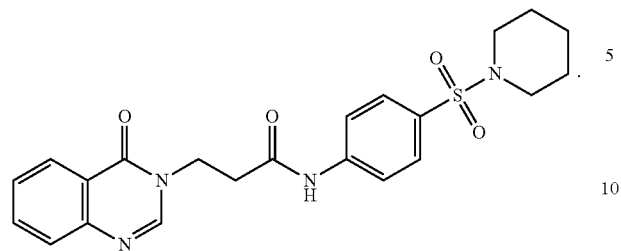
formula I
2. The method according to claim 1, wherein the pharmaceutical composition is administered in a dosage form of an injection.
* * * * *